United States Patent
Tammana et al.

(10) Patent No.: US 9,902,677 B2
(45) Date of Patent: Feb. 27, 2018

(54) LIQUID PHASE OXIDATION OF AROMATIC FEEDSTOCKS WITH MANGANATE RECYCLING TO PRODUCE CARBOXYLIC ACIDS

(71) Applicant: Saudi Arabian Oil Company, Dhahran (SA)

(72) Inventors: Veera Venkata Ramakrishna Tammana, Dhahran (SA); Kareemuddin M. Shaik, Dhahran (SA); Guillaume Robert Jean-Francois Raynel, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 63 days.

(21) Appl. No.: 15/184,398

(22) Filed: Jun. 16, 2016

(65) Prior Publication Data

US 2016/0289156 A1 Oct. 6, 2016

Related U.S. Application Data

(62) Division of application No. 14/104,571, filed on Dec. 12, 2013, now Pat. No. 9,388,110.

(51) Int. Cl.
*B01J 8/00* (2006.01)
*B01J 8/08* (2006.01)
(Continued)

(52) U.S. Cl.
CPC .......... *C07C 51/295* (2013.01); *B01J 8/006* (2013.01); *B01J 8/085* (2013.01); *B01J 19/0046* (2013.01);
(Continued)

(58) Field of Classification Search
CPC ..... B01J 8/00; B01J 8/005; B01J 8/006; B01J 8/08; B01J 8/085; B01J 19/00;
(Continued)

(56) References Cited

U.S. PATENT DOCUMENTS 2,245,528 A 6/1941 Loder
2,833,816 A 5/1958 Saffer et al.
(Continued)

FOREIGN PATENT DOCUMENTS

EP 0181127 B1 2/1991
EP 0164402 B1 4/1993
(Continued)

OTHER PUBLICATIONS

International Search Report and Written Opinion dated Mar. 31, 2015 pertaining to International Application No. PCT/US2014/068053.
(Continued)

*Primary Examiner* — Natasha Young
(74) *Attorney, Agent, or Firm* — Dinsmore & Shohl, LLP

(57) ABSTRACT

Systems and methods for liquid-phase oxidation of an aromatic feedstock containing at least one oxidizable aromatic compound may incorporate an oxidation reactor, a separation apparatus in fluidic communication with the oxidation reactor, a solids treatment unit, and a product recovery unit in fluidic communication with the separation apparatus. The oxidation reactor may conduct liquid-phase oxidation of the oxidizable aromatic compound in the aromatic feedstock in the presence of a manganate salt to form a slurry containing liquid product and solid manganese dioxide. The separation apparatus may accept the slurry from the oxidation reactor and separate the liquid component from the solid component. The solids treatment unit accepts the solid component from the separation apparatus,
(Continued)

treats the solid component with a basic liquid to oxidize the manganese dioxide in the solid component and form a regenerated manganate salt, which may be recycled back to the oxidation reactor.

8 Claims, 2 Drawing Sheets

(51) Int. Cl.
| | |
|---|---|
| *B01J 19/00* | (2006.01) |
| *B01J 19/24* | (2006.01) |
| *C07C 51/00* | (2006.01) |
| *C07C 51/285* | (2006.01) |
| *C07C 51/295* | (2006.01) |
| *C07C 63/04* | (2006.01) |
| *C07C 63/06* | (2006.01) |
| *C07C 63/14* | (2006.01) |
| *C07C 63/15* | (2006.01) |
| *C07C 63/16* | (2006.01) |
| *C07C 63/24* | (2006.01) |
| *C07C 63/26* | (2006.01) |

(52) U.S. Cl.
CPC ..... *C07C 51/285* (2013.01); *B01J 2219/0059* (2013.01); *B01J 2219/0072* (2013.01); *B01J 2219/00599* (2013.01); *B01J 2219/00759* (2013.01)

(58) Field of Classification Search
CPC .............. B01J 19/0046; B01J 19/24; B01J 2219/00274; B01J 2219/00583; B01J 2219/0059; B01J 2219/00599; B01J 2219/00718; B01J 2219/0072; B01J 2219/00759; C07C 51/00; C07C 51/16; C07C 51/285; C07C 51/295; C07C 63/00; C07C 63/04; C07C 63/06; C07C 63/14–63/16; C07C 63/24; C07C 63/26

See application file for complete search history.

(56) References Cited

U.S. PATENT DOCUMENTS

| | | | |
|---|---|---|---|
| 3,406,196 A | 10/1968 | Lewis et al. | |
| 3,410,897 A | 11/1968 | Motoo et al. | |
| 4,117,080 A | 9/1978 | Kawasaki et al. | |
| 5,292,934 A * | 3/1994 | Sikkenga | C07C 51/255 |
| | | | 562/413 |
| 5,958,821 A | 9/1999 | Ishii et al. | |
| 6,355,835 B1 | 3/2002 | Kulsrestha et al. | |
| 7,285,677 B1 | 10/2007 | Yen | |
| 7,692,036 B2 | 4/2010 | Wonders et al. | |
| 2002/0183546 A1 | 12/2002 | Sheppard et al. | |
| 2006/0047155 A1 | 3/2006 | Wonders et al. | |
| 2011/0184208 A1* | 7/2011 | Fraga-Dubreuil | C07C 51/265 |
| | | | 562/418 |

FOREIGN PATENT DOCUMENTS

| | | |
|---|---|---|
| GB | 642459 A | 9/1950 |
| GB | 745159 A | 2/1956 |
| GB | 892766 A | 3/1962 |
| WO | 2007029956 A1 | 3/2007 |

OTHER PUBLICATIONS

Ambulgekar et al., "Oxidation of alkylarenes using aqueous potassium permanganate under cavitation: comparison of acoustic and hydrodynamic techniques", Ultrasonics Sonochemistry 12, pp. 85-90, 2005.
Manufacturing Processes (2007).

* cited by examiner

US 9,902,677 B2

LIQUID PHASE OXIDATION OF AROMATIC FEEDSTOCKS WITH MANGANATE RECYCLING TO PRODUCE CARBOXYLIC ACIDS

CROSS-REFERENCE TO RELATED APPLICATION

This application is a divisional of U.S. patent application Ser. No. 14/104,571, now U.S. Pat. No. 9,388,110, filed Dec. 12, 2013, which is incorporated by reference herein in its entirety.

BACKGROUND

Field

The present specification generally relates to systems and methods for producing aromatic carboxylic acids and, more specifically, to systems and methods for producing aromatic carboxylic acids from aromatic feedstocks by a liquid-phase oxidation in the presence of a potassium manganate oxidizing agent that is regenerated and recycled by the systems and during the methods.

Technical Background

Aromatic carboxylic acids are large-scale commodity chemicals often produced by oxidizing aromatic compounds that have been derived from petroleum fractions. Terephthalic acid, also known as 1,4-benzenedicarboxylic acid, for example, is widely produced in various degrees of purity by oxidation of p-xylene (1,4-dimethylbenzene). Billions of tons of terephthalic acid are produced in this manner annually for principal end use as a precursor to polyethylene terephthalate, a material used for clothing and plastic bottles.

On the bench scale, oxidation of aromatic compounds such as p-xylene is readily carried out by exposing the aromatic compounds to strong oxidizing agents such as permanganate ($MnO_4^-$; Mn(VII)) compounds or dichromate ($Cr_2O_7^{2-}$; Cr(VI)) compounds. The bench-scale process proves unworkable in medium-scale or large-scale industrial processes, however, because solid byproducts such as $MnO_2$ or various chromates are formed in sizable amounts. Such solid byproducts are detrimental to the environment and, therefore, require high disposal costs if they are merely discarded as waste on the industrial scale.

Current commercial manufacturing of aromatic carboxylic acids such as terephthalic acid, for example, may involve one or more of complex catalyst systems, acidic media, or bromine sources. These chemistries tend to be corrosive, so as to necessitate the use of expensive reactors made of metals such as titanium. There remain ongoing needs for oxidation technologies for aromatic compounds that may avoid corrosive media that necessitate expensive reactors, that may exhibit high conversions to usable product, and that may avoid environmental concerns by limiting or eliminating solid waste byproducts.

SUMMARY

According to various embodiments, systems are provided for liquid-phase oxidation of an aromatic feedstock containing at least one oxidizable aromatic compound. The systems may include an oxidation reactor, a separation apparatus in fluidic communication with the oxidation reactor, a solids treatment unit in fluidic communication with the separation apparatus and the oxidation reactor, an alkali stream in fluidic communication with the solids treatment unit, and a product recovery unit in fluidic communication with the separation apparatus. The oxidation reactor may be adapted to conduct liquid-phase oxidation of the at least one oxidizable aromatic compound in the aromatic feedstock to a carboxylate in the presence of a manganate salt in an alkaline medium to form a slurry comprising a liquid component containing the carboxylate and a solid component containing manganese dioxide. The separation apparatus may accept the slurry from the oxidation reactor and may separate the liquid component from the solid component. The product recovery unit may accept the liquid component from the separation apparatus. The solids treatment unit may accept the solid component from the separation apparatus, may treat the solid component with a basic liquid from the alkali stream to oxidize the manganese dioxide in the solid component and form a regenerated manganate salt, and may send at least a portion of the regenerated manganate salt back to the oxidation reactor.

According to further embodiments, methods are provided for oxidizing an aromatic feedstock containing at least one oxidizable aromatic compound. The methods may include oxidizing the at least one oxidizable aromatic compound of the aromatic feedstock in an oxidation reactor in an oxidation medium comprising a manganate salt in an alkaline medium to form a slurry comprising a liquid component containing a carboxylate and a solid component containing manganese dioxide. The methods may further include separating the slurry in a separation apparatus that is in fluidic communication with a solids treatment unit and a product recovery unit. The liquid component may be transferred to the product recovery unit, and the solid component may be transferred to the solids treatment unit. The methods may further include contacting the solid component in the solids treatment unit with a basic liquid to oxidize the manganese dioxide in the solid component and form a regenerated manganate salt. The methods may further include recycling at least a portion of the regenerated manganate salt from the solids treatment unit back to the oxidation reactor.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawing.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
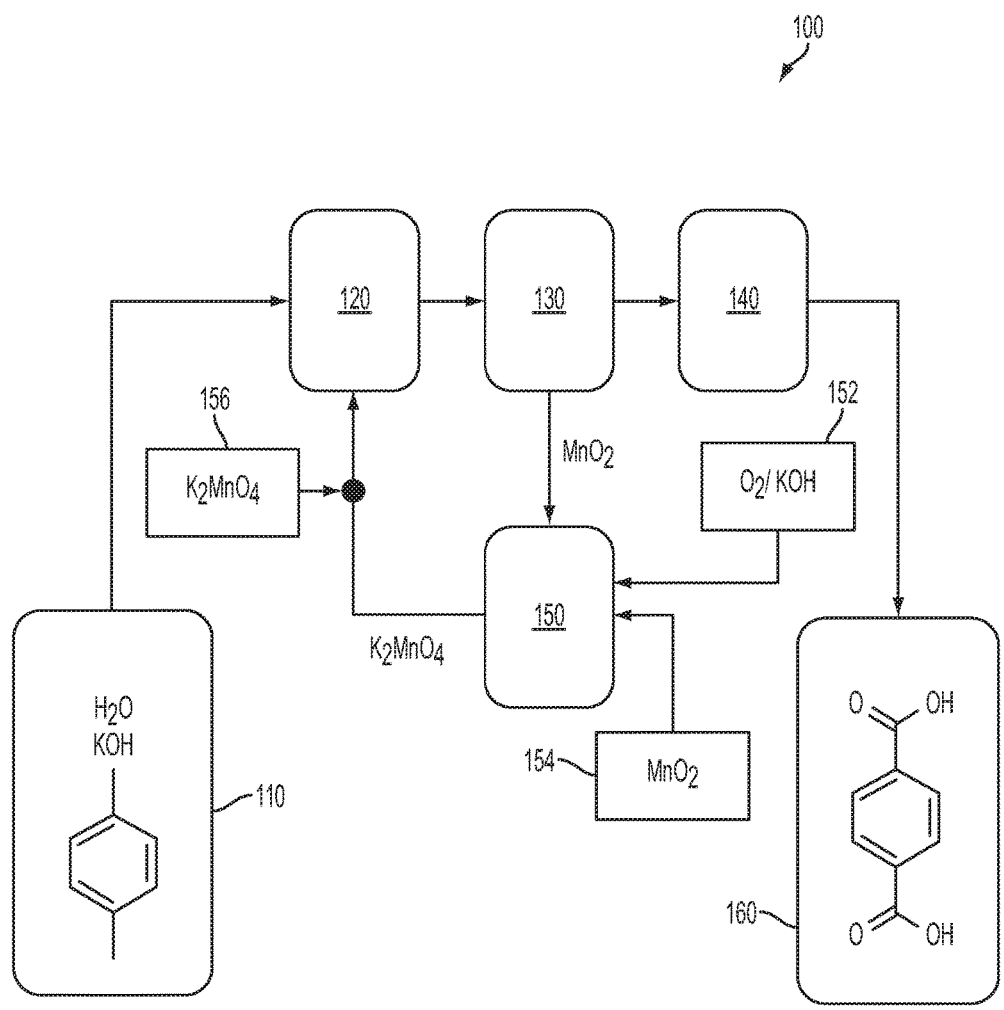
FIG. 1 is a schematic representation of an exemplary system for liquid-phase oxidation of an aromatic feedstock containing at least one oxidizable aromatic compound according to embodiments described herein.

Definitions of various chemical compounds and moieties, as applicable to systems and methods described in embodiments herein, will now be provided. Various embodiments of systems for liquid-phase oxidation of an aromatic feedstock containing at least one oxidizable aromatic compound, and also various embodiments of methods for oxidizing an aromatic feedstock containing at least one oxidizable aromatic compound, will be discussed in detail below.

As used herein, the term "aromatic compound" refers to a monocyclic or polycyclic, unsaturated compound having preferably from 3 to 25 carbon atoms, preferably from 5 to 16 carbon atoms, more preferably from 6 to 14 carbon atoms, each of which may be substituted or unsubstituted. Aromatic compounds may include compounds that contain at least one planar ring having p-orbitals perpendicular to the plane of the ring at each ring atom and satisfying the Hückel rule where the number of pi electrons in the ring is (4n+2), where n is an integer. Aromatic compounds may contain a single aromatic ring or may comprise two or more aromatic rings, for instance two or more fused aromatic rings. Single-ring aromatic compounds typically may have 6 or 10 ring atoms. For aromatic compounds with two or more fused rings, each ring typically has 4, 5, 6, 7, or 8 ring atoms. An example of such an aromatic compound is bicyclo[6,2,0] decapentane, which is an 8-membered ring fused to a 4-membered ring and has 10 delocalized electrons in conformance with the Hückel rule, where n=2. In some embodiments, the aromatic compound is monocyclic. The aromatic compound may include one or more carbocyclic rings, one or more heterocyclic aromatic rings, or a combination of one or more carbocyclic rings and one or more heterocyclic aromatic rings. Non-limiting examples of heterocyclic aromatic rings are rings containing 1, 2, or 3 heteroatoms selected from N, O and S. Non-limiting examples of aromatic compounds include benzene, naphthalene, anthracene, phenanthrene, pyrene, benzopyrene, and ring-substituted derivatives of these.

As used herein, the term "alkyl group" refers to a saturated, straight chain (i.e., unbranched) or branched aliphatic hydrocarbon that is optionally substituted with one or more functional groups.

As used herein, unless defined otherwise according to context, the term "oxidizable group" refers to a chemical moiety that, when substituted onto a ring carbon atom of an aromatic compound, is capable of being oxidized in one or more steps to form at least one group that includes a carboxylate, a carboxylic acid, or a direct precursor to a carboxylate or carboxylic acid such as a formyl group, for example.

Further non-limiting examples of oxidizable groups include alkyl groups, specifically $C_1$ to $C_6$ alkyl groups or $C_1$ to $C_3$ alkyl groups, aldehydes, ketones, alcohol groups, ester-protected alcohol groups, amines, thioketones, thioaldehydes, and thiols. Further non-limiting examples of oxidizable groups include alkanediyl groups that attach to two ring carbon atoms, such that the alkanediyl forms a ring. Such a ring may be oxidized to form two carboxylic acid groups. Typically, to be capable of being oxidized in one or more steps to form at least one group that includes a carboxylate, a carboxylic acid, or a direct precursor to a carboxylate or carboxylic acid, alkyl-type oxidizable groups will possess at least one alpha hydrogen atom (for example, a benzylic hydrogen if the aromatic compound contains a benzene ring) bonded to a carbon atom of the oxidizable group that is itself directly bonded to the ring carbon atom of the aromatic compound. Thus, while methyl, ethyl, propyl, 1-methylethyl, or 2-methylethyl groups are oxidizable group attached to benzene due to the presence at least one benzylic hydrogen, a 1,1-dimethylethyl (tert-butyl) group is not an oxidizable group when attached to benzene, because it lacks a benzylic hydrogen.

As used herein, the term "oxidizable aromatic compound" refers specifically to an aromatic compound, as defined above, in which at least one ring carbon is substituted with an oxidizable group, as defined above. In some embodiments herein, oxidizable aromatic compounds may include one, two, three, or more than three ring carbons that are substituted with an oxidizable group. Oxidation of oxidizable aromatic compounds to form carboxylate groups or carboxylic acids from the oxidizable group or groups may occur in one step or in multiple mechanistic steps, such that any intermediate compounds formed in multi-step processes are also encompassed by the foregoing definition of oxidizable aromatic compound.

In some embodiments, oxidizable aromatic compounds may have generic formula (I) or (II), which both depict exemplary oxidizable groups bonded to aromatic moieties of aromatic compounds according to the definition above herein:

In generic formula (I), the group A is an aromatic moiety of the aromatic compound that is bonded to an oxidizable group —$CR^1R^2H$. In generic formula (II), the group A is an aromatic moiety that is bonded to an oxidizable group —$C(=R^1)H$. In both generic formulas (I) and (II), groups $R^1$ and $R^2$ may be the same or different and may be chosen in non-limiting embodiments from alkyl groups, O, S, —OH, H, —SH, ester groups —$OR^3$ where $R^3$ is alkyl, and amines. It should be understood that the generic formulas (I) and (II) are provided to illustrate only a single oxidizable group and that one or more additional oxidizable groups, such as one, two, three, four, or more than four additional oxidizable groups may be attached to the aromatic moiety A. For example, p-xylene (1,4-dimethyl benzene) is an example of a molecule according to formula (I), in which benzene is the aromatic moiety A and two methyl groups (i.e., —$CH_3$, formula (I) with $R^1$=$R^2$=—H) are oxidizable groups attached to the aromatic moiety. When oxidized, the oxidizable groups according to generic formulas (I) or (II) both form a carboxylate of formula (III):

The carboxylate of formula (III) may be in solution with an available counteranion such as sodium or potassium, for example, or may be worked up with an acid such as sulfuric acid, for example, to form a carboxylic acid.

Non-limiting examples of oxidizable aromatic compounds include alkyl-substituted, aldehyde-substituted, ketone-substituted, alcohol-substituted, ester-protected alcohol-substituted, amine-substituted, thioketone-substituted, thioaldehyde-substituted, and thiol-substituted aromatic compounds such as benzenes, naphthalenes, anthracenes, phenanthrenes, pyrenes, or benzopyrenes. Non-limiting examples of alkyl-substituted benzenes may include monoalkylbenzenes such as toluene (methylbenzene) or ethylbenzene; dialkylbenzenes such as xylenes (dimethylbenzene isomers), diethylbenzene isomers, and ethylmethylbenzene isomers; and trialkylbenzenes such as trimethylbenzene isomers, triethylbenzene isomers, ethyldimethylbenzene isomers, or diethylmethylbenzene isomers. It should be understood that oxidizable aromatic compounds according to the above definition may be further substituted by additional groups that are not oxidizable groups, provided that at least one ring carbon is substituted with an oxidizable group. Thus, a compound such as a chloromethylbenzene isomer is an "oxidizable aromatic compound" because the methyl group is an oxidizable group, even though the chloro substitution is not. Likewise, a dichlorobenzene is not an oxidizable aromatic compound according to the above definition, because its only substitutions are two chloro groups, neither of which is an oxidizable group.

As used herein, the term "aromatic carboxylic acid" refers to an aromatic compound in which at least one carboxylic acid group (—COOH) is attached directly to a ring carbon of the aromatic compound. The aromatic carboxylic acid may contain one or more carboxylic acid groups attached directly to an aromatic group. In some embodiments, aromatic carboxylic acids may contain one, two, or three carboxylic acid groups. In other embodiments, aromatic carboxylic acids may contain at least two carboxylic acid groups. In other embodiments, aromatic carboxylic acids may contain exactly one carboxylic acid group, exactly two carboxylic acid groups, or exactly three carboxylic acid groups. Non-limiting examples of aromatic carboxylic acids according to embodiments herein may include benzoic acid (from toluene, for example), terephthalic acid (from p-xylene, for example), isophthalic acid (from m-xylene, for example), phthalic acid (from o-xylene, for example), trimellitic acid (from pseudocumene, i.e., 1,2,4-trimethylbenzene, for example), and naphthalene dicarboxylic acids (from various isomers of dimethylnaphthalene, for example).

The terms "manganate" and "permanganate" refer to manganese-containing anions and are used according to their customarily understood definition. The term manganate may be used interchangeably with its chemical notation $MnO_4^{2-}$, which describes a species containing manganese atom in a 6+ oxidation state. The term permanganate may be used interchangeably with its chemical notation $MnO_4^-$, which describes a species containing manganese atom in a 7+ oxidation state. Thus, the compound potassium manganate ($K_2MnO_4$), which is a potassium salt of the manganate anion, is to be clearly distinguished from potassium permanganate ($KMnO_4$), which is a potassium salt of the permanganate anion. Potassium manganate may be formed by reacting manganese dioxide ($MnO_2$) with potassium hydroxide (KOH) in the presence of oxygen or air. Potassium permanganate ($KMnO_4$) may be prepared from potassium manganate ($K_2MnO_4$) by an energy intensive process such as electrolytic oxidation in alkaline media, boiling in the presence of oxygen, or treating with oxidants stronger than the $KMnO_4$ such as lead dioxide ($PbO_2$) or sodium bismuthate ($NaBiO_3$), for example.

Reference will now be made in detail to embodiments of systems for liquid-phase oxidation of an aromatic feedstock containing at least one oxidizable aromatic compound. Referring to FIG. 1, the system 100 according to some embodiments may include an oxidation reactor 120, a separation apparatus 130 in fluidic communication with the oxidation reactor 120, a solids treatment unit 150 in fluidic communication with the separation apparatus 130 and the oxidation reactor 120, an alkali stream 152 in fluidic communication with the solids treatment unit 150, and a product recovery unit 140 in fluidic communication with the separation apparatus 130. The oxidation reactor 120 may be adapted to conduct liquid-phase oxidation of the at least one oxidizable aromatic compound in the aromatic feedstock 110 to a carboxylate in the presence of a manganate salt in an alkaline medium to form a slurry comprising a liquid component containing the carboxylate and a solid component containing manganese dioxide. The separation apparatus 130 may accept the slurry from the oxidation reactor 120 and may separate the liquid component from the solid component. The product recovery unit 140 may accept the liquid component from the separation apparatus 130. The solids treatment unit 150 may accept the solid component from the separation apparatus 130, may treat the solid component with a basic liquid from the alkali stream 152 to oxidize the manganese dioxide in the solid component and form a regenerated manganate salt, and may send at least a portion of the regenerated manganate salt back to the oxidation reactor 120. Various embodiments of methods for oxidizing an aromatic feedstock 110 containing at least one oxidizable aromatic compound will be discussed in detail below. In some embodiments, the methods may be performed using a system 100 according to embodiments described herein.

The system 100 for liquid-phase oxidation in general converts an aromatic feedstock 110 containing at least one oxidizable aromatic compound, shown by way of illustration and not by way of limitation in FIG. 1 as p-xylene, into a carboxylate or carboxylic acid, shown in FIG. 1 as terephthalic acid to be consistent with the p-xylene oxidizable aromatic compound and not by way of limitation.

The oxidation reactor 120 may be any vessel of any size and material suitable for conducting a liquid-phase oxidation of the at least one oxidizable aromatic compound in a basic oxidation medium at a desired output. The basic oxidation medium may contain the oxidizable aromatic compound, water, a base, and a manganate salt as the oxidizing agent. The base may be any basic compound that furthers the oxidation of the oxidizable aromatic compound in the potassium manganate. Preferred bases include metal hydroxides, particularly alkali-metal hydroxides such as sodium hydroxide, potassium hydroxide, or mixtures thereof. In some embodiments, and as shown in FIG. 1, the base may be potassium hydroxide. Though in FIG. 1 potassium manganate is shown in an exemplary embodiment, the manganate salt may be any metal manganate and preferably is an alkali-metal manganate such as sodium manganate or potassium manganate. The aromatic feedstock 110, and particularly the oxidizable aromatic compound contained in the aromatic feedstock 110, may be derived from any practical source such as a petroleum fraction. In some embodiments, the aromatic feedstock 110 contains only one oxidizable aromatic compound in a substantially purified form. In other embodiments, the aromatic feedstock 110 may contain more than one oxidizable aromatic compound, any or all of which may be oxidized by the system 100. The aromatic feedstock may reside in the oxidation reactor 120 at a suitable oxidation temperature for a suitable reaction time to produce a slurry. The slurry may contain a liquid component and a solid component. The liquid component may contain an oxidized product formed from the oxidizable aromatic compound, such as a carboxylate, for example. The solid component may contain manganese dioxide ($MnO_2$), which forms as a result of the reduction of the manganate salt, for example, potassium manganate ($K_2MnO_4$), when the oxidizable aromatic compound is oxidized.

The separation apparatus 130 is in fluidic communication with the oxidation reactor 120 and may accept the slurry from the oxidation reactor 120 and separate the liquid component of the slurry from the solid component of the slurry. The separation apparatus may be any type of device used in industrial processes for separating solid components and liquid components in a process stream. For example, the separation apparatus 130 may be a filtration apparatus that operates gravimetrically, or with the aid of sonication, vibration, agitation, centrifugation, or any combination thereof. The separation apparatus 130 may contain internal components such as filters that allow the liquid component to pass through which the solid component is left behind.

The product recovery unit 140 is in fluidic communication with the separation apparatus 130. Therefore, the product recovery unit 140 may accept the liquid component from the separation apparatus 130. The liquid component contains the oxidized product that has been formed from the oxidizable aromatic compound. The oxidized product may be a carboxylate, typically in combination with a counterion such as potassium, which has been derived from the base, the manganate salt (particularly when potassium manganate is used), or both. The product recovery unit 140 may be any type of vessel of suitable size, shape, and material, in which an acid workup can be performed on the liquid component formed from the oxidizable aromatic compound. The product recovery unit 140 may be connected to an acid stream that delivers acid to the product recovery unit 140 or may be at least partially filled with an acid. Thereby, when the liquid component is received in the product recovery unit 140, the oxidized product such as the carboxylate may be protonated and, thereby, fully converted to the desired product 160, a carboxylic acid, shown in an illustrative manner as terephthalic acid in FIG. 1. The desired product 160 may then be removed from or pumped out of the system 100 for any further processing that may be necessary such as separation, purification, distillation, for example.

The solids treatment unit 150 is in fluidic communication with the separation apparatus 130 and the oxidation reactor 120. The solids treatment unit 150 may accept the solid component from the separation apparatus 130. The solid component may be transferred from the separation apparatus 130 to the solids treatment unit 150 by any industrially feasible method such as by simply conveying the solid component or by suspending the solid component in a rinsing liquid and pumping the solid component and the rinsing liquid together. The solid component contains the manganese dioxide ($MnO_2$), which represents depleted manganate salt. In the solids treatment unit 150 the solid component, specifically the $MnO_2$, may be treated with a basic liquid from an alkali stream 152. In some embodiments, the basic liquid may contain or consist of potassium hydroxide (KOH). Additionally, oxygen ($O_2$) or air may be introduced into the solids treatment unit 150 through the alkali stream 152 or otherwise. Oxidation of $MnO_2$ to form a regenerated manganate salt such as potassium manganate ($K_2MnO_4$), for example, readily occurs in potassium hydroxide in the presence of oxygen, particularly at temperatures above 406° C. It should be understood, however, that other basic liquids and oxidation conditions for converting the $MnO_2$ may be possible, and that the combination of KOH and $O_2$ or air is provided as exemplary only.

At least a portion of the regenerated manganate salt formed in the solids treatment unit 150 may be sent back to the oxidation reactor 120 for further participation in oxidizing the oxidizable aromatic compound. In some embodiments, the system 100 may include a supplemental manganese dioxide source 154 to add additional manganese dioxide to the $MnO_2$ already in the solids treatment unit 150, thereby ensuring a sufficient amount of manganate salt is available for recycling back to the oxidation reactor 120. In other embodiments, the system 100 may include a supplemental oxidant source 156 fluidically coupled to the system 100 between the solids treatment unit 150 and the oxidation reactor 120. The supplemental oxidant source 156 may add additional manganate salt to the portion of regenerated potassium manganate flowing back to the oxidation reactor 120, also ensuring a sufficient amount of manganate salt is available in the oxidation reactor 120. The supplemental oxidant source 156 may also add some permanganate salt, such as potassium permanganate ($KMnO_4$), for example, to the portion of regenerated manganate salt flowing back to the oxidation reactor 120, which increases the oxidation strength of the liquid flowing back to the oxidation reactor 120. In such embodiments, after performing as an oxidizing agent in the oxidation reactor 120, the permanganate salt, along with the manganate salt, is reduced to $MnO_2$, which subsequently can be recycled back to manganate salt.

The system 100 according to embodiments described above may be used to oxidize a variety of oxidizable aromatic compounds to form a variety of desired products 160 such as carboxylic acids, for example. In some embodiments, the at least one oxidizable aromatic compound may be chosen from monomethylbenzenes, dimethylbenzenes, trimethylbenzenes, monomethylnaphthalenes, and dimethylnaphthalenes. In other embodiments, the at least one oxidizable aromatic compound may be chosen from p-xylene, m-xylene, o-xylene, pseudocumene, 2,6-dimethylnaphthalene, 1,5-dimethylnaphthalene, or 2,7-dimethylnaphthalene. In other embodiments, the at least one oxidizable aromatic compound may be chosen from p-xylene, m-xylene, o-xylene, p-toluic acid, m-toluic acid, o-toluic acid, and combinations thereof. In still other embodiments, the at least one oxidizable aromatic compound may include p-xylene, which forms as a carboxylic acid product, terephthalic acid, after acid workup on a carboxylate species such as benzene-1,4-dicarboxylate in the product recovery unit 140.

Thus, the system 100 according to the embodiments described above, an economically and environmentally benign manganate salt such as potassium manganate ($K_2MnO_4$), for example, may be used as an oxidizing agent for oxidizable aromatic compounds in a basic medium with fewer technical concerns than comparable processes requiring corrosive, acidic media. Moreover, the system 100 addresses and surmounts the significant difficulty with regard to handling or disposal of precipitated $MnO_2$ from the oxidation reaction by regenerating the $MnO_2$ to easily form manganate salt that is recycled back to the oxidation reactor 120.

Having described above several embodiments of systems for liquid-phase oxidation of an aromatic feedstock containing at least one oxidizable aromatic compound, various embodiments of methods for oxidizing an aromatic feedstock containing at least one oxidizable aromatic compound will now be described. In some embodiments, the methods may be performed using a system according to embodiments described above.

Referring to FIG. 1 with regard to components of the system 100 that may be applicable to methods for oxidizing an aromatic feedstock, the methods for oxidizing an aromatic feedstock 110 containing at least one oxidizable aromatic compound may include oxidizing the at least one oxidizable aromatic compound of the aromatic feedstock in an oxidation reactor 120 in an oxidation medium comprising a manganate salt in an alkaline medium to form a slurry comprising a liquid component containing a carboxylate and a solid component containing manganese dioxide. The methods may further include separating the slurry in a separation apparatus 130 that is in fluidic communication with a solids treatment unit 150 and a product recovery unit 140. The liquid component may be transferred to the product recovery unit 140, and the solid component may be transferred to the solids treatment unit 150. The methods may further include contacting the solid component in the solids treatment unit with a basic liquid to oxidize the manganese dioxide in the solid component and form a regenerated manganate salt. The methods may further include recycling at least a portion of the regenerated manganate salt from the solids treatment unit 150 back to the oxidation reactor 120.

The aromatic feedstock 110 may contain at least one oxidizable aromatic compound, water, and a base such as potassium hydroxide or other suitable alkali. The aromatic feedstock may be introduced into the oxidation reactor 120 as a multiphasic mixture, or the components of the aromatic feedstock 110 may be introduced into the oxidation reactor 120 separately. The aromatic feedstock 110 may then be combined with a manganate salt such as potassium manganate ($K_2MnO_4$), for example, as the oxidizing agent in the oxidation reactor 120 to begin the oxidation process. In alternative embodiments, the feedstock 110 may be combined with a mixture of the manganate salt and a permanganate salt as the oxidizing agent. In such embodiments, the weight ratio of the manganate salt to the permanganate salt may range from about 1:1 to about 1000:1, or from about 10:1 to about 1000:1, or from about 100:1 to about 1000:1. In some embodiments, pure or substantially pure oxidizable aromatic compound may be introduced first into the oxidation reactor 120, and subsequently aqueous base (such as aqueous KOH, for example) may be added slowly to the oxidizable aromatic compound in combination with a stoichiometric amount of the manganate salt. The oxidation may be conducted at atmospheric pressure at a suitable temperature range such as from about 60° C. to about 80° C. for a suitable reaction time such as from about 4 hours to about 6 hours. During the oxidation reaction, the at least one oxidizable aromatic compound is oxidized to a carboxylate, and the manganate salt is reduced to solid manganese dioxide ($MnO_2$). The combination of the carboxylate and the $MnO_2$ may be in the form of a slurry having the carboxylate in a liquid component of the slurry and the $MnO_2$ in a solid component of the slurry.

Figure 2:
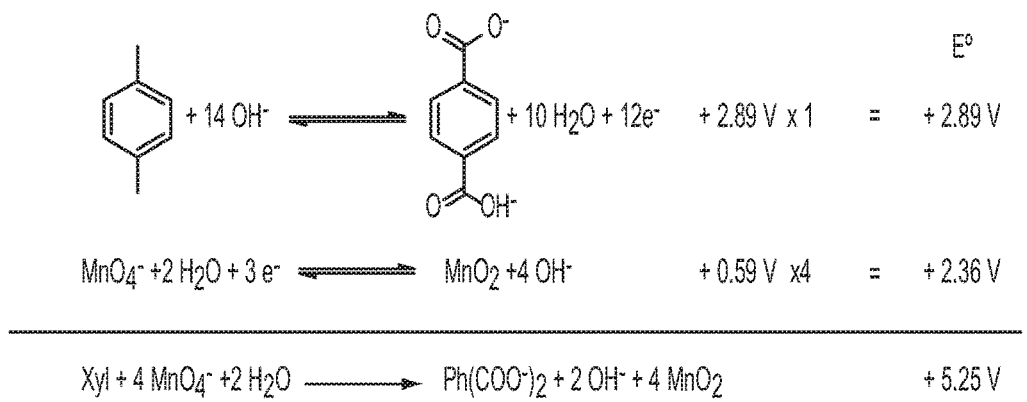
FIG. 2 shows calculations for predicting electrochemical potential values for p-xylene oxidation to terephthalic acid using permanganate ($MnO_4^-$.

Without intent to be bound by theory, it is believed that the oxidation reaction of the at least one oxidizable aromatic compound occurs readily and spontaneously in the presence of the manganate salt and the base such as KOH. In FIG. 2, calculations are provided for electrochemical potential in the oxidation of p-xylene to terephthalic acid using potassium permanganate ($KMnO_4$), a reaction commonly performed in bench-scale oxidations p-xylene and used here as a basis for comparison only. In particular, with an oxidation using the very strong oxidizing agent $KMnO_4$, alkyl groups attached to aromatic molecules such as benzene and having at least one benzyl hydrogen are easily oxidized to carboxylic acids at mild temperatures and atmospheric pressure. The feasibility of this reaction can be elucidated using Equation (I).

$$\Delta G = -nFE \quad (I)$$

In Equation (I), $\Delta G$ is the change in Gibbs free energy, n is the number of electrons transferred, F is the Faraday constant, and E is the electrochemical potential available from the redox reactions considered. Typically, it is understood that a redox reaction having known values for n, F, and E will be spontaneous (an exergonic reaction) if $\Delta G$ is negative or E is positive and will not be spontaneous (an endergonic reaction) if $\Delta G$ is positive or E is negative. Thus, the positive value of E=+5.25 V from the calculation in FIG. 2 indicates the oxidation reaction for p-xylene to terephthalic acid in $KMnO_4$ is spontaneous and readily occurs. Even so, this reaction also produces manganese dioxide, which is expensive to dispose and raises environmental concerns. Though it is possible to reprocess the $MnO_2$ byproduct all the way to potassium permanganate ($KMnO_4$) for reuse, such a reprocessing would require two steps: first, by contacting the $MnO_2$ to KOH and oxygen to form potassium manganate ($K_2MnO_4$), then by electrochemically processing the $K_2MnO_4$ to form $KMnO_4$. The electrochemical processing of $K_2MnO_4$ to $KMnO_4$ typically involves a sacrificial electrode, which itself is additional waste to be disposed of. As such, embodiments of the method for oxidizing the aromatic feedstock include recycling the $MnO_2$ as $K_2MnO_4$, without further oxidation of $K_2MnO_4$ to $KMnO_4$ which has been demonstrated above to be a feasible.

Figure 3:
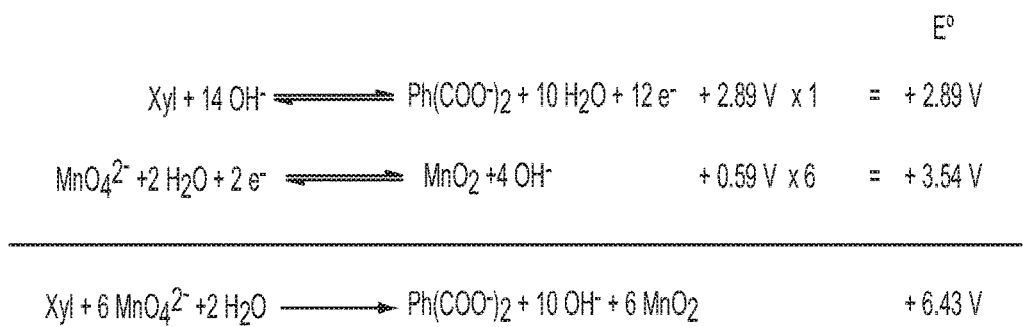
FIG. 3 shows calculations for predicting electrochemical potential values for p-xylene oxidation to terephthalic acid using manganate ($MnO_4^{2-}$).

Even though in theory $KMnO_4$ could be reprocessed and recycled, a recycling of $K_2MnO_4$ used as the oxidizing agent is far less energy intensive. Moreover, in an oxidation reaction, it is believed that the milder $K_2MnO_4$ may lead to fewer potential reaction impurities than a similar process involving $KMnO_4$. The electrochemical calculations for oxidation of p-xylene to terephthalic acid in the presence of potassium manganate ($K_2MnO_4$) are provided in FIG. 3. It can be readily ascertained that the positive value for E=+6.43 V with $K_2MnO_4$ is in fact higher than the value of +5.25 V with $KMnO_4$. As such, it is believed that the higher electrochemical potential of the $K_2MnO_4$ reaction indicates that $K_2MnO_4$ is a more efficient oxidation reagent than $KMnO_4$ for oxidizing oxidizable aromatic compounds, such as the exemplary p-xylene.

In the methods for oxidizing the aromatic feedstock containing the at least one oxidizable aromatic compound, the slurry formed in the oxidation reactor 120 may be separated in a separation apparatus 130 that is in fluidic communication with a solids treatment unit 150 and a product recovery unit 140. The slurry may be transferred to the separation apparatus 130 by any practicable method. In the separation apparatus 130, the solid component of the slurry, which contains $MnO_2$, is separated from the liquid component of the slurry, which contains oxidized aromatic compound, typically in the form of a carboxylate or carboxylate salt. The liquid component may then be transferred to the product recovery unit 140, and the solid component may be transferred to the solids treatment unit 150.

The methods for oxidizing the aromatic feedstock containing the at least one oxidizable aromatic compound may further include contacting the solid component in the solids treatment unit 150 with an amount of a basic liquid sufficient to oxidize the manganese dioxide ($MnO_2$) in the solid component and form a regenerated manganate salt such as potassium manganate ($K_2MnO_4$), for example. The contacting of the solid component with the basic liquid may be conducted in the presence of oxygen or air, either of which may be introduced into the solids treatment unit 150 through a suitable conduit or introduction mechanism.

The methods for oxidizing the aromatic feedstock containing the at least one oxidizable aromatic compound may further include recycling at least a portion of the regenerated manganate salt from the solids treatment unit 150 back to the oxidation reactor 120. Optionally, the amount of manganate salt being sent back to the oxidation reactor 120 may be adjusted to ensure an adequate supply of the manganate salt. In one embodiment, the methods may further include adding supplemental manganate salt to the portion of the regenerated potassium manganate being sent back to the oxidation reactor 120. Optionally, the addition of supplemental manganate salt to the portion of the regenerated potassium manganate being sent back to the oxidation reactor 120 may further include adding an amount of permanganate salt such as potassium permanganate ($KMnO_4$), for example, to the supplemental manganate salt, so as to increase the oxidizing power of the oxidizing agent in the oxidation reactor 120. The supplemental manganate salt may be added to the stream of regenerated manganate salt being sent from the solids treatment unit 150 to the oxidation reactor 120. In other embodiments, the methods may further include adding supplemental manganese dioxide to the manganese dioxide received from the separation apparatus 130 and being oxidized in the solids treatment unit 150, so as to increase the amount of manganate salt to be sent back to the oxidation reactor 120 from the solids treatment unit 150.

The methods for oxidizing the aromatic feedstock containing the at least one oxidizable aromatic compound may further include recovering the desired product 160 from the product recovery unit 140. Optionally, before the desired product 160 is recovered, the methods may further include performing an acid workup on the carboxylate in the product recovery unit to form a carboxylic acid. In illustrative embodiments, the acid workup may be performed by treating the carboxylate with an acid such as sulfuric acid, which protonates the carboxylate groups to form carboxylic acids. Once the carboxylates are protonated, the desired product 160 may precipitate from solution and be separated from any remaining liquids to be recovered. In some embodiments, the methods may include post-treatments to the desired product 160 that has been recovered including, for example, purification, recrystallization, distillation, or separation.

The methods described in the embodiments above may be used to oxidize a variety of oxidizable aromatic compounds contained in the aromatic feedstock 110 introduced into the oxidation reactor 120, to form a variety of desired products 160 such as carboxylic acids, for example. In some embodiments, the at least one oxidizable aromatic compound may be chosen from monomethylbenzenes, dimethylbenzenes, trimethylbenzenes, monomethylnaphthalenes, and dimethylnaphthalenes. In other embodiments, the at least one oxidizable aromatic compound may be chosen from p-xylene, m-xylene, o-xylene, pseudocumene, 2,6-dimethylnaphthalene, 1,5-dimethylnaphthalene, or 2,7-dimethylnaphthalene. In other embodiments, the at least one oxidizable aromatic compound may be chosen from p-xylene, m-xylene, o-xylene, p-toluic acid, m-toluic acid, o-toluic acid, and combinations thereof. In still other embodiments, the at least one oxidizable aromatic compound may include p-xylene, which forms as a carboxylic acid product, terephthalic acid, after acid workup on a carboxylate species such as benzene-1,4-dicarboxylate in the product recovery unit 140.

Thus, the methods according to the embodiments described above, particularly the methods employing a system 100 according to embodiments described herein, such as the system of FIG. 1, allow for an economically and environmentally benign manganate salts such as potassium manganate ($K_2MnO_4$), for example, to be used as an oxidizing agent for oxidizable aromatic compounds in a basic medium with fewer technical concerns than comparable processes requiring corrosive, acidic media, complex catalyst systems that are difficult to regenerate, and further corrosive bromine radical initiators. Moreover, the methods described herein address and surmount the significant difficulties with regard to handling or disposal of precipitated $MnO_2$ from the oxidation reaction by regenerating the $MnO_2$ to easily re-form manganate salt ($K_2MnO_4$, for example) that is recycled back to the oxidation reactor 120.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A system for liquid-phase oxidation of an aromatic feedstock containing at least one oxidizable aromatic compound, the system comprising:
    an oxidation reactor;
    a separation apparatus in fluidic communication with the oxidation reactor;
    a solids treatment unit in fluidic communication with the separation apparatus and the oxidation reactor; and
    an alkali stream in fluidic communication with the solids treatment unit; and
    a product recovery unit in fluidic communication with the separation apparatus,
wherein:
    the oxidation reactor is adapted to conduct liquid-phase oxidation of the at least one oxidizable aromatic compound in the aromatic feedstock to a carboxylate in the presence of a manganate salt in an alkaline medium to form a slurry comprising a liquid component containing the carboxylate and a solid component containing manganese dioxide;
    the separation apparatus accepts the slurry from the oxidation reactor and separates the liquid component from the solid component;
    the product recovery unit accepts the liquid component from the separation apparatus;
    the solids treatment unit accepts the solid component from the separation apparatus, treats the solid component with a basic liquid from the alkali stream to oxidize the manganese dioxide in the solid component and form a regenerated manganate salt, and sends at least a portion of the regenerated manganate salt back to the oxidation reactor.

2. The system of claim 1, further comprising a supplemental manganate source in fluidic communication with the solids treatment unit and the oxidation reactor, the supplemental manganate source providing supplemental manganate salt to the portion of the regenerated manganate salt being sent back to the oxidation reactor.

3. The system of claim 1, further comprising a supplemental manganese dioxide source in fluidic communication with the solids treatment unit, the supplemental manganese dioxide source providing supplemental manganese dioxide to the manganese dioxide being oxidized to increase an amount of manganate salt to be sent back to the oxidation reactor.

4. The system of claim 1, wherein the separation apparatus is a filtration apparatus.

5. The system of claim 1, wherein the product recovery unit is in fluidic communication with an acid stream that is combined with the carboxylate to form a carboxylic acid from the carboxylate.

6. The system of claim 1, wherein the at least one oxidizable aromatic compound is chosen from monomethylbenzenes, dimethylbenzenes, trimethylbenzenes, monomethylnaphthalenes, and dimethylnaphthalenes.

7. The system of claim 1, wherein the at least one oxidizable aromatic compound is chosen from chosen from p-xylene, m-xylene, o-xylene, and combinations thereof.

8. The system of claim 1, wherein the at least one oxidizable aromatic compound comprises p-xylen and the carboxylate comprises a benzene-1,4-dicarboxylate.

* * * * *

UNITED STATES PATENT AND TRADEMARK OFFICE
CERTIFICATE OF CORRECTION

PATENT NO.         : 9,902,677 B2
APPLICATION NO.    : 15/184398
DATED              : February 27, 2018
INVENTOR(S)        : Veera Venkata et al.

Page 1 of 1

It is certified that error appears in the above-identified patent and that said Letters Patent is hereby corrected as shown below:

Column 13, Line 22, Claim 7:
"oxidizable aromatic compound is chosen from chosen from"
Should read:
--oxidizable aromatic compound is chosen from--.

Column 13, Line 25, Claim 8:
"oxidizable aromatic compound comprises p-xylen and the"
Should read:
--oxidizable aromatic compound comprises p-xylene and the--; and Signed and Sealed this
Thirteenth Day of November, 2018

Andrei Iancu
*Director of the United States Patent and Trademark Office*